United States Patent [19]

Imonti

[11] Patent Number: 5,098,416
[45] Date of Patent: Mar. 24, 1992

[54] SYRINGE ADAPTER ASSEMBLY FOR WITHDRAWING AND COLLECTING BODY FLUID

[75] Inventor: Maurice M. Imonti, Dana Point, Calif.

[73] Assignee: Nestle, S.A., Switzerland

[21] Appl. No.: 633,175

[22] Filed: Dec. 28, 1990

Related U.S. Application Data

[63] Continuation of Ser. No. 272,819, Nov. 18, 1988, abandoned.

[51] Int. Cl.⁵ .............................. A61M 1/00
[52] U.S. Cl. .................... 604/319; 604/187; 604/240; 604/902
[58] Field of Search ............ 604/22, 35, 73, 119, 604/120, 131, 187, 190, 240-243, 283, 317-319, 321, 322, 326, 902, 905; 128/749, 752, 753, 758, DIG. 1

[56] References Cited

U.S. PATENT DOCUMENTS

| | | | |
|---|---|---|---|
| 2,522,108 | 9/1948 | Flagg | 604/319 |
| 3,395,705 | 8/1968 | Hamilton | 604/119 |
| 3,889,682 | 6/1975 | Denis et al. | 604/119 |
| 4,255,096 | 3/1981 | Coker, Jr. et al. | 128/DIG. 1 |
| 4,266,815 | 5/1981 | Cross | 604/905 |
| 4,314,560 | 2/1982 | Hefgott et al. | 604/35 |
| 4,393,879 | 7/1983 | Milogram | 604/119 |
| 4,468,217 | 8/1984 | Kuzmick et al. | 604/902 |
| 4,607,868 | 8/1986 | Harvey et al. | 604/243 |
| 4,639,019 | 1/1987 | Mittleman | 604/283 |
| 4,755,365 | 10/1988 | Swartz | 604/119 |
| 4,813,931 | 3/1989 | Hauze | 604/319 |

FOREIGN PATENT DOCUMENTS

| | | | |
|---|---|---|---|
| 0154985 | 5/1952 | Australia | 604/240 |
| 0077539 | 10/1974 | Canada | 128/276 |
| 2581546 | 5/1985 | France | 604/187 |
| WO88/06900 | 9/1988 | PCT Int'l Appl. | 604/187 |
| 2142827 | 1/1985 | United Kingdom | 604/131 |

Primary Examiner—John D. Yasko
Assistant Examiner—Anthony Gutowski
Attorney, Agent, or Firm—Lowe, Price, LeBlanc & Becker

[57] ABSTRACT

An improved apparatus and system for withdrawing and collecting body fluids is disclosed. The system includes an adapter which is arranged to cooperate with a handheld aspirator apparatus and a syringe assembly having an open end portion. The adapter includes a sealing asembly which engages the interior of the syringe assembly and a barrier which is insertable into the syringe assembly to prevent clogging, but permit body fluid aspiration.

12 Claims, 2 Drawing Sheets

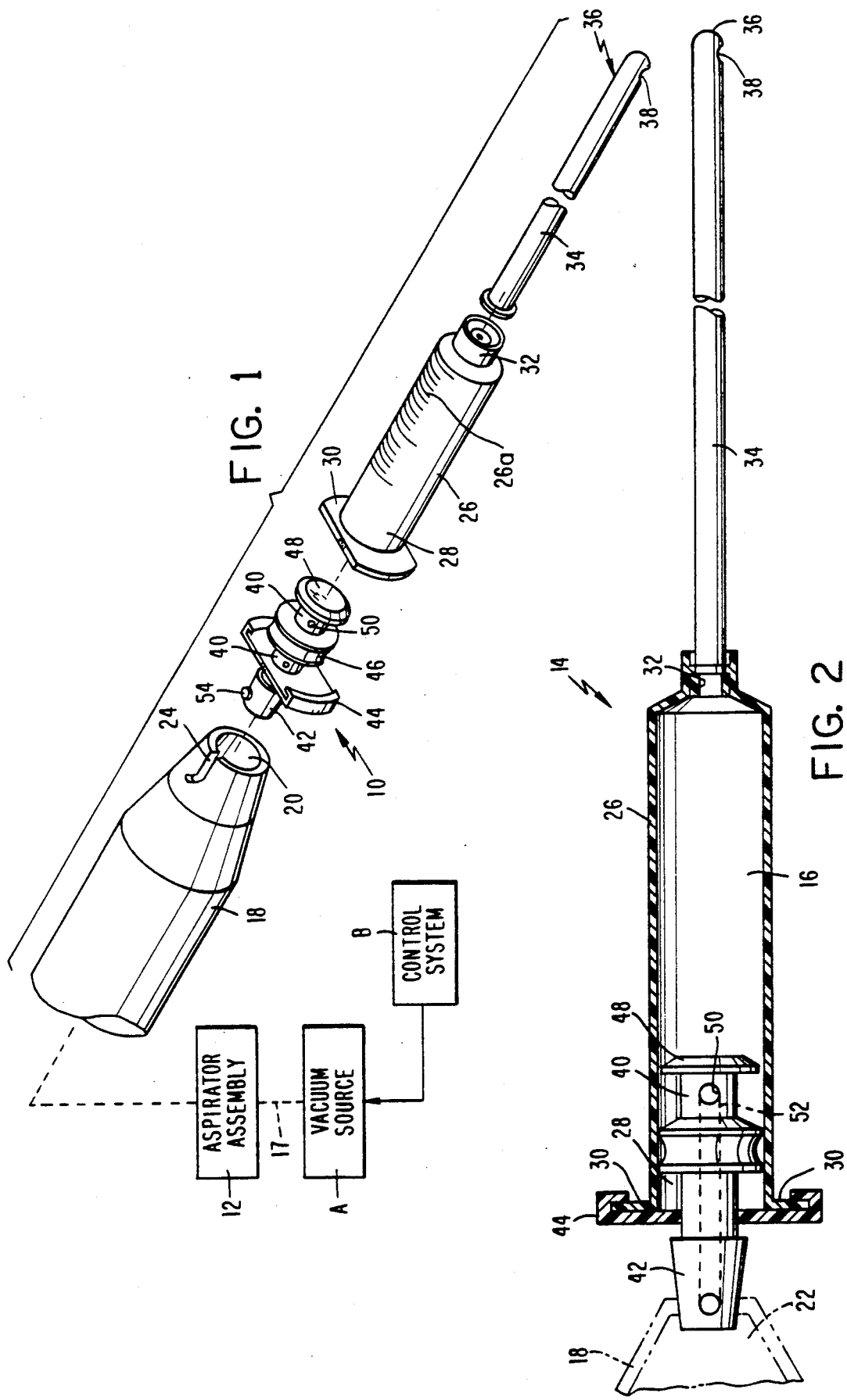

SYRINGE ADAPTER ASSEMBLY FOR WITHDRAWING AND COLLECTING BODY FLUID

This application is a continuation of now abandoned application, Ser. No. 07/272,819 filed on Nov. 18, 1988, now abandoned.

BACKGROUND OF THE INVENTION

The present invention relates generally to withdrawing and collecting body fluids from any body part through the use of an improved system and apparatus and method therefor.

A number of approaches are known for withdrawing body fluids. Syringes are the most common device. One type includes a syringe barrel having attached to a distal end portion thereof a hypodermic needle for penetrating the body. Fluid withdrawal occurs by reason of negative pressure being generated in the barrel in response to manual pulling of a piston-like plunger in the barrel. Another type of syringe for draining body cavities is generally referred to as a bulb type. Such type includes a resiliently compressible bulbous portion attached to one end of a barrel. When the bulbous portion is squeezed negative pressure is created in the barrel for purposes of withdrawing fluid. There are several problems generally associated with this kind of device including leakage between the bulbous portion and the barrel and the general inability to successfully control the creation of a partial vacuum on a consistent basis. Moreover, the volume of fluid withdrawn is limited by the size of the syringe body. This volume limitation may unnecessarily prolong a fluid withdrawal procedure.

It is also known to use mechanized devices for aspirating body tissue and fluids from body cavities. Exemplary apparatus useful in this connection are described in the following U.S. Pat. Nos: 3,526,219; 3,589,363; 4,223,676; and 4,493,694. The aspiration is in response to a partial vacuum created by a vacuum system. This vacuum system creates a partial vacuum at an operative tip inserted into a body, which tip is ultrasonically vibrated. These patents are, however, primarily concerned with the aspiration of small amounts of body tissue and irrigation of body fluids incident to an ultrasonic surgery operation. Also, these prior devices do not provide for an operator being able to quickly and easily control collection of predetermined amounts of body fluid at the body site whereat the fluid is being withdrawn.

None of the known prior art, however, shows or suggests a system, a method and an adapter whereby a syringe assembly is coupled to an aspirator assembly for purposes of controlling the withdrawal and collection of body fluids in the syringe assembly.

SUMMARY OF THE INVENTION

It is an object of the present invention to improve known body fluid withdrawal and collection procedures. According to this invention provision is made for an adapter assembly for use in selectively coupling an aspirator assembly to a syringe assembly. The aspirator assembly includes a fluid aspiration passageway and the syringe assembly has an open end portion thereof. In an illustrated embodiment, the adapter assembly comprises means for removably coupling the adapter assembly to the aspiration passageway of the aspirator assembly. The adapter assembly includes means for removably coupling it to the open end portion of the syringe assembly. For fluidically communicating the syringe assembly and the aspirator apparatus provision is made for means for facilitating aspiration of body fluids therethrough. The adapter assembly includes means for sealing an interior of the syringe assembly for preserving at least a partial vacuum therein and for preventing leakage of body fluids from the syringe assembly.

In an illustrated embodiment of the adapter assembly provision is made for means for defining a barrier which is insertable in the open end portion of the syringe assembly to prevent viscous material clogging the fluidic communicating means but permitting aspiration of body fluids to the fluid communicating means.

In another illustrated embodiment of the adapter assembly provision is for the means for releasably coupling the adapter assembly to the syringe assembly having gripping portions, each of which releasably grips flange portions of the syringe assembly.

Further according to this invention provision is made for an improved system for withdrawing and collecting fluid. The system includes means for inducing at least a partial vacuum; a syringe assembly including a syringe housing having an open end thereof; and an aspirator assembly coupled to the inducing means. The aspirator assembly includes means for facilitating aspiration of body fluids through at least a portion thereof. Included in the system is an adapter assembly for use in selectively coupling the aspirator assembly to the syringe assembly. The adapter assembly comprises means for removably coupling the adapter assembly to the aspirator assembly and means for removably coupling the adapter assembly to the syringe assembly. The adapter assembly includes means for fluidically communicating the interior of the syringe assembly and the aspirator assembly for facilitating aspiration of body fluids therethrough. Provision is made for means for controlling the vacuum inducing means for controlling aspiration so that preselected amounts of body fluids can be withdrawn into the syringe assembly.

The present invention contemplates a method of controlling and collecting aspirated body fluids. The method includes the steps of using a fluid collecting vessel having a device directly coupled thereto which is insertable into a body cavity and capable of withdrawing body fluid in response to aspiration; and automatically aspirating body fluid into the fluid collecting vessel and controlling the amount of fluid withdrawn by controlling the aspiration of the body fluid.

Among the other objects and features of the present invention are the provisions of an improved adapter assembly system and method for withdrawing and collecting body fluids; the provisions of an improved system, adapter assembly and method for facilitating controlled withdrawal and collection of body fluids; the provisions of a significantly versatile method and system for withdrawing body fluids from any portion of the body; the provision of aspirating body fluids into a syringe assembly adjacent the site of body fluid withdrawal, whereby the amount of fluid withdrawn can be more easily and accurately determined and controlled and, the provision of storing the withdrawn body fluid in a syringe for reuse.

Still other objects and further scope of applicability of the present invention will become apparent from the detailed description to follow when taken in conjunction with the accompanying drawings in which like

BRIEF DESCRIPTION OF THE DRAWINGS

FIG. 1 is a partially diagrammatic and partially perspective view of the improved adapter apparatus and system of the present invention;

FIG. 2 is a sectional view of an adapter assembly and syringe assembly used in the present invention;

DETAILED DESCRIPTION

Figure 4:
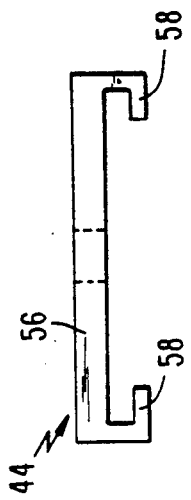
FIG. 4 is a plan view of a syringe coupling member.

FIG. 1 illustrates an adapter assembly 10 made in accordance with the principles of the present invention. The adapter assembly 10 essentially removably couples an aspirator apparatus 12, schematically depicted, to a syringe assembly 14. As will be explained, the adapter assembly 10 establishes fluid communication between the aspirator assembly 12 and an interior chamber 16 (FIG. 2) of the syringe assembly 14. A partial vacuum is created by suitable vacuum source, such as a peristaltic pump, schematically depicted and designated by reference character A. The vacuum source A generates the partial vacuum for aspirating body fluid from the body through the syringe assembly 14, adapter assembly 10, aspirator assembly 12 and suitable tubing 17 (indicated by dotted lines) to a collection container (not shown).

The aspirator assembly 12 does not, per se, form an aspect of the present invention, hence a detailed description thereof is omitted. Only those portions of the aspirator assembly 12 necessary for purposes of understanding the present invention will be set forth. The aspirator assembly 12 is of a type similar to one described in U.S. Pat. No. 4,784,649 issued Nov. 15, 1988 and is assigned to the Cooper Companies, Inc. This patent is incorporated herein by reference to provide a more detailed description of the basic components and operation of the aspirator assembly 12. Within the scope of the present invention it will be appreciated, of course, that the aspirator assembly 12 need not be of this particular type but others can be used as well. Such an aspirator assembly 12 include a handpiece (not shown) which facilitates a procedurist using the same for purposes of withdrawing body fluid from any body portion. The aspirator assembly 12 can include a projecting hollow tip portion 18 having a suitably sized opening 20 formed at the distal end thereof which leads to aspiration passageway 22 which fluidically communicates, through structure in the handpiece (not shown), with the vacuum source A. Formed at the distal end of the hollow tip 18 is a female type luer slot 24 (FIG. 1).

The vacuum source A can be of the type described in the aforenoted patent. In this regard, aspiration can be controlled by means of a manually controlled valve assembly (not shown) included in the aforenoted aspirator assembly 12. Manipulation of the valve assembly will appropriately commence and cease aspiration of the body fluids. The vacuum source A can also be a highly controllable peristaltic pump. In this latter case, the vacuum source A could be controlled by a known type of vacuum control means or system B. The control system B can control the duration and value of the partial vacuum. The control system B selectively effects commencement and cessation of the partial vacuum so that a procedurist may stop withdrawal of a desired amount of body fluid through the operation of a foot pedal or the like. The control system B is understood in the art, thereby requiring no further explanation. For example, such a control system is available from CooperVision, Inc. of Irvine, Calif. Of course other kinds of control systems are envisioned by this invention.

Reference is now made to the syringe assembly 14. It should be pointed out that the syringe assembly 14 is but on of several which may be used within the spirit and scope of this invention. The syringe assembly 14 includes a hollow collection vessel or body portion 26 made of for example, a transparent medical grade plastic. The body portion 26 also has volume markings 26a thereon indicative of the volume of body fluid withdrawn. With the syringe assembly 14 being upstream of an aspirator assembly 12, an operator can easily determine and control the amount of fluid withdrawn. The body 26 has formed adjacent an enlarged open end portion 28 thereof a pair of finger grip portions 30 extending radially outwardly therefrom. A reduced open end portion 32 extends from the forward portion of the body 26 and is sized and shaped so as to tightly receive therein and limit inward axial movement of a suction cannula 34. While a suction cannula 34 is depicted, it will be understood of course, that this invention contemplates the use of hypodermic needles. Of course the body 26 would have other structure for joining of the hypodermic needle thereto. The suction cannula 34 has a rounded distal end portion 36 and adjacent thereto a suction port 38 for aspirating body fluid therethrough. It should be noted that whether a hypodermic needle or a suction cannula is used, largely depends on the type of fluid to be withdrawn and part of the body to be aspirated.

Figure 5:
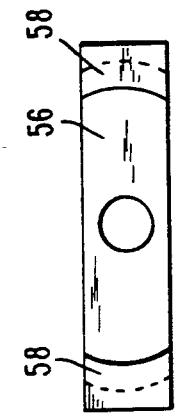
FIG. 5 is an elevational view of the syringe coupling member shown in FIG. 4.
Figure 3:
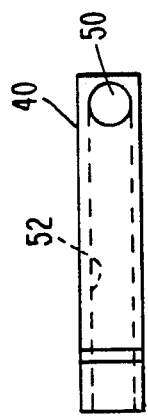
FIG. 3 is an elevational view of tubular member of the adapter assembly of the present invention.

Reference is made back again to the adapter assembly 10 (FIGS. 1-5) As depicted, the adapter assembly 10 includes a central tubular member 40, luer type adapter 42, syringe locking device 44, vacuum stop or seal 46 and viscous material barrier 48.

The tubular member 40 has a suction port 50 adjacent one end thereof which communicates with a passage 52 extending therethrough to provide fluid communication between syringe chamber 16 and the aspiration passageway 22. The luer adapter 42 has a pin 54 which extends radially outwardly and is slidably received in the slot 24 so as to removably couple the adapter assembly 10 to the aspirator assembly 12. The luer adapter 42 has a truncated conical configuration which is sized to fit snuggly within the opening 20 (FIG. 2). The luer adapter 42 provides coupling means for the adapter assembly 10.

The syringe locking device 44 includes a apertured plate 56 which is press fit on the tubular member 40. Extending outwardly of the plate are hooked finger gripping portions 58 which are adapted to slidably cooperate in a frictional manner with the finger grips 30 (See FIG. 2). The syringe locking device 44 provides means for releasably coupling the adapter assembly 10 to the syringe assembly 14. To do this the finger grips 30 and the finger gripping portions 58 are relatively rotated with respect to each other so that the finger gripping portions 58 securely hold the finger grips 30.

The present invention contemplates other structure for releasably coupling the adapter assembly 10 to a syringe assembly 14 and an aspirator assembly 12.

The vacuum seal 46 is mounted on the tubular member 40 and serves to maintain the partial vacuum within the chamber 16 as well as prevent the body fluid leaking from the chamber. The vacuum seal 46 is an elastomeric member which is sized and configured to slidably and sealingly engage the interior of the body 26.

The viscous material barrier 48 is affixed to the forward end of the tubular member 40 and is dimensioned to facilitate continued aspiration of body fluid and minimize blockage of viscous material clogging the suction port 50.

After the foregoing detailed description, it is believed the operation of the present invention is selfevident. However to supplement such description, it will be appreciated that the aspirator assembly 12 is connected to a vacuum source A, such as a peristaltic pump. The source A is controlled by the control system B in a manner well-understood in the art so that the amount of the partial vacuum and the commencement and cessation of the partial vacuum may be selectively controlled by the operator as, for example, a function of the fluid in the syringe body 26. Accordingly, an operator can selectively cease the aspiration when a desired amount of fluid is collected. This is more accurate than known approaches. The amount of fluid can remain in the syringe for reuse. Also the procedurist can continously aspirate the fluid to a collection vessel. Thus, fluid can be continuously withdrawn and the withdrawal procedure is, therefore, not limited by the volume of syringe body.

It will be appreciated that the present invention contemplates that the adapter assembly 10 can be made from a wide variety materials. Such structure can be made of plastic if it is desired that they are to be disposed. Also, the materials can be autoclavable if they are desired for reuse.

Certain changes may be made in the above described system and apparatus without departing from the scope of the present invention herein involved. It is intended that all matter contained in the description and shown in the accompanying drawings shall be interpreted as illustrative and not in a limiting sense.

What is claimed is:

1. A removably insertable adapter assembly for use in selectively coupling an aspirator assembly to a syringe assembly, the aspirator assembly including a fluid aspiration passageway, the syringe assembly including an open end barrel housing portion thereof, and flange portions on said barrel housing adjacent said open end, said adapter assembly comprising:
    means for removably coupling said adapter assembly to the aspiration passageway of the aspirator assembly;
    means for removably coupling said adapter assembly to the flange portions at the open end barrel housing portion of the syringe assembly;
    means for fluidically communicating the syringe assembly and the aspirator assembly for facilitating aspiration of body fluids therethrough;
    means for sealingly engaging an interior of the syringe barrel housing portion for preserving at least a partial vacuum therein and for preventing leakage of body fluids from the syringe assembly; and
    means for defining a barrier which is insertable through the open end barrel housing portion of the syringe assembly so as to substantially prevent viscous material clogging said fluidic communicating means but permitting continuing aspiration of body fluids to said communicating means.

2. The adapter assembly of claim 1 wherein:
    said means for removably coupling said adapter assembly to the syringe assembly includes a pair of opposed finger gripping portions, each of said gripping portions being constructed to releasably frictionally engage said flange portions of the syringe assembly.

3. The adapter of claim 1, wherein said means for fluidically communicating said syringe assembly and said aspirator assembly are disposed between said means for defining a barrier and means for sealing.

4. The adapter of claim 1, wherein said means for removably coupling said adapter assembly to said barrel housing portion is disposed between said means for sealing and said means for removably coupling said adapter assembly to said aspiration passageway.

5. A system of controlled withdrawal and collection of body fluids comprising:
    means for inducing at least a partial vacuum;
    a syringe assembly including a hollow syringe housing having an open end thereof, flange portions on said housing adjacent said open end and a hollow operative device connected to said housing and adapted to be inserted into an animal or human body to withdraw body fluids therefrom in response to aspiration;
    a handheld aspirator assembly coupled to said inducing means, said aspirator assembly including means for facilitating aspiration of body fluids through at least a portion thereof;
    a removably insertable adapter assembly for sue in selectively coupling said aspirator assembly to said syringe assembly;
    said adapter assembly comprising means for removably coupling said adapter assembly to said aspirator assembly, means for removably coupling and inserting said adapter assembly to said syringe assembly, means for fluidically communicating the hollow syringe housing to said aspirator assembly for facilitating aspiration of body fluids therethrough;
    means for controlling sad inducing means for controlling aspiration so that preselected amounts of body fluids can be withdrawn into said syringe housing;
    means on said adapter assembly being insertable into the interior of said syringe housing for sealingly engaging the interior of said syringe housing for preserving at least a partial vacuum therein and for preventing leakage of body fluids from said syringe assembly; and
    means on said adapter assembly for defining a barrier which is insertable into said syringe housing as to prevent viscous material clogging said fluid communicating means but permitting continuing aspiration of body fluids to said communicating means.

6. The system of claim 5 wherein:
    said means for releasably coupling said adapter assembly to said syringe assembly includes gripping portions, each o said gripping portions being constructed to releasably frictionally engage said flange portions of said syringe assembly.

7. The system of claim 5 wherein:
    said syringe assembly includes a hollow and transparent housing having markings indicative of body fluid volume.

8. The system of claim 5, wherein said means for fluidically communicating said syringe housing and said aspirator assembly are disposed between said means for defining a barrier and means for sealing.

9. The system of claim 5, wherein said means for removably coupling and inserting said adapter assembly to said syringe assembly portion is disposed between said means for sealing and said means for removably coupling said adapter assembly to said aspiration assembly.

10. A system of controlled withdrawal and collection of body fluids comprising:

means for inducing at least a partial vacuum;

a syringe assembly including a hollow syringe housing having an open end thereof, flange portions on said housing adjacent said open end and a hollow operative device connected to said housing and adapted to be inserted into an animal or human body to withdraw body fluids therefrom in response to aspiration;

a handheld aspirator assembly coupled to said inducing means, said aspirator assembly including means for facilitating and controlling aspiration of body fluids through at least a portion thereof;

an adapter assembly for use in selectively coupling said aspirator assembly to said syringe assembly; said adapter assembly comprising means for removably coupling said adapter assembly to said aspirator assembly, means for removably coupling said adapter assembly to said syringe assembly, means for fluidically communicating the hollow syringe housing to said aspirator assembly for facilitating aspiration of body fluids therethrough;

means on said adapter assembly for sealingly engaging an interior of the syringe assembly for preserving at least a partial vacuum therein and for preventing leakage of body fluids form the syringe assembly; and means on said adapter assembly for defining a barrier which is insertable through the open end portion of the syringe assembly so as to substantially prevent viscous material clogging said fluidic communicating means but permitting continuing aspiration of body fluids to said communicating means.

11. The system of claim 10, wherein said means for fluidically communicating said hollow syringe housing and said aspirator assembly are disposed between said means for defining a barrier and means for sealing.

12. The system of claim 10, wherein said means for removably coupling said adapter assembly to said syringe assembly is disposed between said means for sealing and said means for removably coupling said adapter assembly to said aspirator assembly.

* * * * *